United States Patent [19]

Foster

[11] Patent Number: 5,015,250
[45] Date of Patent: May 14, 1991

[54] MEDICAL INSTRUMENT FOR DRIVING A SUTURE NEEDLE

[75] Inventor: Thomas L. Foster, Poland, Ind.

[73] Assignee: Vance Products Incorporated, Spencer, Ind.

[21] Appl. No.: 464,347

[22] Filed: Jan. 12, 1990

[51] Int. Cl.$^5$ ............................................. A61B 17/00
[52] U.S. Cl. ...................................... 606/147; 606/148
[58] Field of Search ................................ 606/145–150

[56] References Cited

U.S. PATENT DOCUMENTS

| 1,539,221 | 5/1925 | Tennant | 606/147 |
|---|---|---|---|
| 2,363,334 | 11/1944 | Jones | 606/147 |
| 3,871,379 | 3/1975 | Clarke | 606/148 |
| 3,921,640 | 11/1975 | Freeborn | 128/ |
| 4,326,531 | 4/1982 | Shimonaka | 128/ |
| 4,406,237 | 9/1983 | Eguchi et al. | 112/169 |
| 4,417,532 | 11/1983 | Yasukata | 112/169 |
| 4,424,898 | 1/1984 | Thyen et al. | 206/ |
| 4,440,171 | 4/1984 | Nomoto et al. | 606/145 |
| 4,484,580 | 11/1984 | Nomoto et al. | 606/146 |
| 4,491,135 | 6/1985 | Klein | 606/147 |
| 4,524,771 | 6/1985 | McGregor et al. | 128/ |
| 4,572,185 | 2/1986 | Rich | 606/145 |
| 4,580,567 | 4/1986 | Schweitzer et al. | 606/147 |
| 4,624,252 | 11/1986 | Weiss | 128/ |
| 4,765,334 | 8/1988 | Weiss | 128/ |
| 4,827,929 | 5/1989 | Hodge | 128/ |

OTHER PUBLICATIONS

Semm, K., *Pelviscopy-Operative Guidelines*, D-2300 Kiel 1-F.R.G., 1988, pp. 52–53.

*Primary Examiner*—Stephen C. Pellegrino
*Assistant Examiner*—Gary Jackson
*Attorney, Agent, or Firm*—Richard J. Godlewski

[57] ABSTRACT

A needle driver instrument suitable for use with a trocar sheath in operative endoscopic surgical procedures such as laparoscopic and pelviscopic procedures is disclosed for driving a curved suture needle. The needle driver instrument comprises an elongated cylindrical tube member having a channel formed about the distal end thereof for receiving either a curved or a straight suture needle. The channel is transversely formed through the elongated member and has a plurality of surfaces to orient and fix the suture needle in a predetermined orientation. A wedge operable across the channel and through the passageway of the elongated member wedges the needle between at least two of the contact surfaces of the channel to fixedly position the suture needle in the desired orientation. At the proximal end of the device is a handle with a generally U-shaped spring extending therefrom for manual operation of the wedge. A rod extending from the wedge through the elongated member of the instrument is connected to the spring for actuation and operation of the wedge. The device is comprised of component parts which are easily disassembled for cleaning and sterilization.

28 Claims, 3 Drawing Sheets

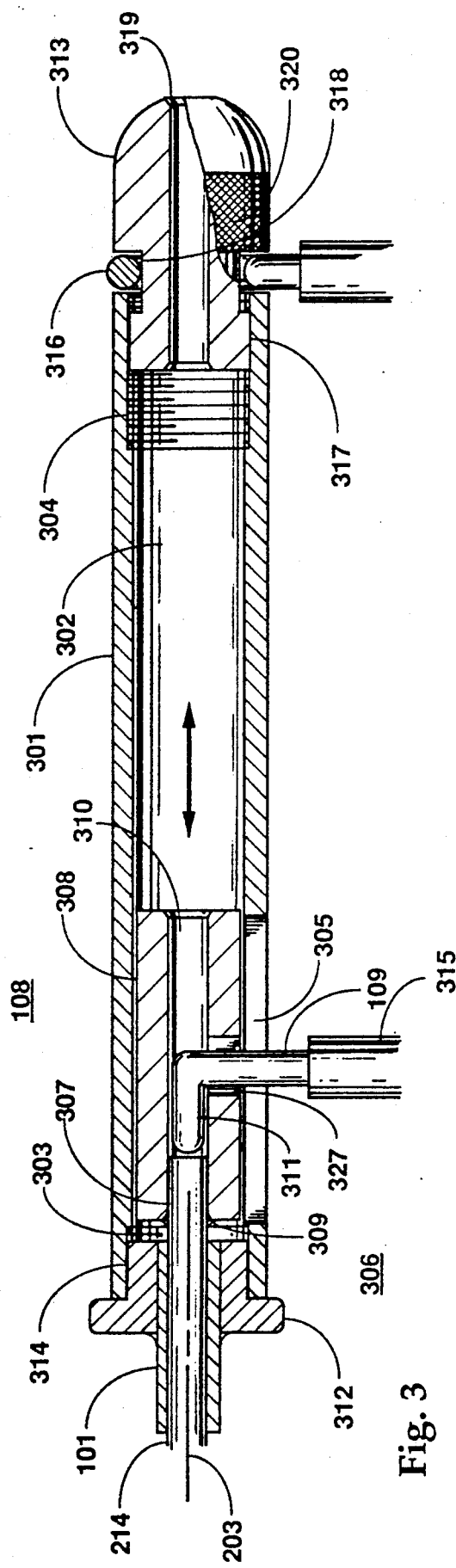
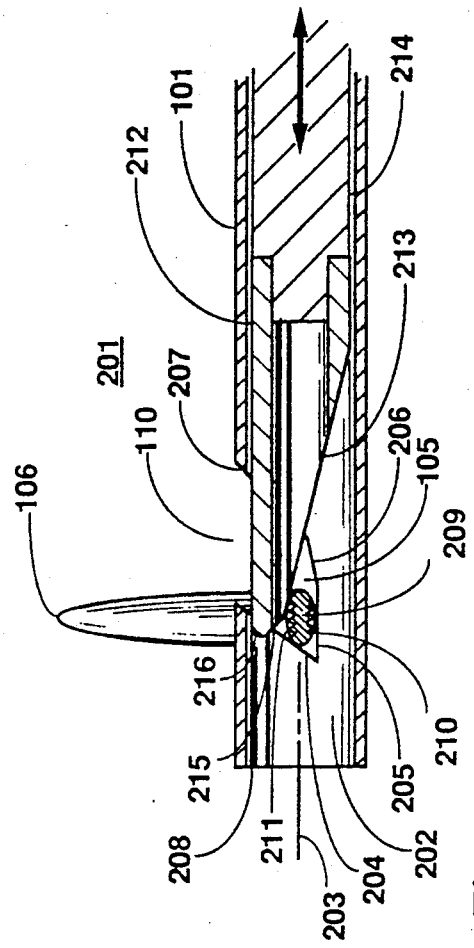
Fig. 3
Fig. 2

MEDICAL INSTRUMENT FOR DRIVING A SUTURE NEEDLE

TECHNICAL FIELD

This invention relates to medical instruments and particularly to medical instruments for driving a suture needle through tissue.

BACKGROUND OF THE INVENTION

A number of manually operated medical and surgical instruments are available for holding or grasping a suture needle. Generally, two varieties of surgical needles are commercially available: straight needles and curved needles. For many situations, straight needles are preferred since they can be more easily handled. In restricted space, the use of a curved needle is preferred. However, curved needles are very difficult to properly manipulate manually and are invariably utilized in conjunction with needle holders specifically designed for use therewith. The most common needle holders include a configuration somewhat like needle-nose pliers with clamping means for locking the gripping jaws thereof in a fixed position.

With even more confined or limited access endoscopic procedures such as operative laparoscopy or pelviscopy where the surgical instruments are typically inserted through a trocar sheath, the size of the suture needle is limited as well as the size of the needle holder which must be inserted through the trocar sheath to the surgical site. Endoscopic needle holders have typically included a pair of opposing jaws positioned at the distal end of an elongated member which is inserted through the trocar sheath. One jaw is commonly held stationary while the opposing jaw is operated between an open and closed position. To better grasp the suture needle, the opposing jaws typically include a plurality of teeth for further grasping the needle.

One problem with these opposing jaw needle holders is the difficulty in maintaining a fixed position when the suture needle is grasped. This problem is further complicated with the use of a curved suture needle which is very common with endoscopic procedures. The curved needle has a tendency to change its position when grasped due to the curvature of the needle. As a result, the surgeon spends considerable time in making just a few sutures with the curved needle.

Another problem is that unless the curved needle is constantly maintained in perfect alignment along its own curvature during suturing, the perforated tissue offers resistance which increases the force necessary to complete the suture. As a result, there is increased tissue trauma with the formation of excessively large openings and possibly even tears in the tissue which may retard proper healing.

A number of curved needle suture devices have been developed for use in invasive type surgery. Such holders commonly have a curved needle affixed to an elongated member for implementing a series of sutures. However, these holders are invariably too bulky to position in restricted surgical site areas and are near impossible to insert through a trocar sheath for endoscopic procedures due to physical size limitations.

SUMMARY OF THE INVENTION

The foregoing problems are solved and a technical advance is achieved with an illustrative medical instrument for use in endoscopic surgical procedures such as operative laparoscopic or pelviscopic procedures for driving a needle through tissue. In particular, this medical instrument is advantageously utilized through a trocar sheath for driving either a straight, or more particularly, a curved suture needle. The medical instrument comprises an elongated member, such as a cylindrical tube, having a longitudinal passageway extending therein and insertable through the trocar sheath. A channel for receiving the suture needle is formed in the elongated member about the distal end thereof and transverse to the passageway. The device also includes a wedge which is positioned within the passageway of the elongated member and operable across the channel to fixedly position the suture needle in a predetermined orientation when positioned in the channel. The channel forms a predetermined number of surfaces in the elongated member which are each capable of making contact with the needle when the needle is positioned in the channel.

The channel surfaces are formed in the elongated member at predetermined angles with respect to the longitudinal axis of the elongated member. One of the contact surfaces is formed in a substantially parallel inclination with respect to the longitudinal axis of the elongated member. Another contact surface is positioned at an approximately 60° angle with respect to the longitudinal axis. Two other surfaces of the channel are used to guide the needle to the first two contact surfaces for positioning with the wedge when operated across the channel.

At the distal end, the wedge includes an engaging segment, such as a tube or rod with a beveled surface. The beveled surface forms an angle of approximately 14° with respect to the longitudinal axis of the elongated member for wedging the suture needle between the parallel and 60° channel surfaces and the beveled surface when the wedge is operated across the channel. This configuration of angles has been found to orient a curved suture needle in the same orientation with respect to the elongated member. The contact surfaces formed in the elongated member and the engaging wedge segment form at least four and as many as six or more contact surfaces with a tubular engaging segment for fixedly positioning a curved suture needle in the same orientation each time the suture needle is grasped.

The wedge also includes an elongated segment such as a rod or linkage tube which extends through the passageway of the elongated member. A handle is attached to the elongated member for manual operation and actuation of the engaging segment of the wedge. The handle includes a larger diameter tubular member connected to the elongated member for receiving the proximal end of the wedge actuating rod.

The handle further advantageously includes a spring for forcing the wedge against and fixedly positioning the curved suture needle in the channel. For easy manual movement of the wedge, the spring extends from the handle passageway in a generally U-shaped configuration with one end connected to the proximal end of the handle and the other attached to the actuating rod for moving the wedge. The U-shaped spring is easily grasped and operated by the physician to move the wedge across the channel and manipulate the curved suture needle positioned therein.

Curved suture needles typically have an elliptically shaped cross sectional area with a series of grooves longitudinally formed in the surface of the needle. The generally, cross-sectional elliptical shape of curved needles and the ridges longitudinally formed on the surface of the needle further facilitate the almost identical positioning of a curved suture needle when inserted and wedged in the channel of the present medical instrument. The ease of movement of the wedge across the channel during an endoscopic surgical procedure significantly decreases the time required by the surgeon required for suturing.

BRIEF DESCRIPTION OF THE DRAWING

FIG. 2 depicts a cross-sectional side view of the distal end of the needle driver instrument of FIG. 1;

FIG. 3 depicts a partial cross-sectional side view of the proximal end of the needle driver instrument of FIG. 1;

DETAILED DESCRIPTION

Figure 1:
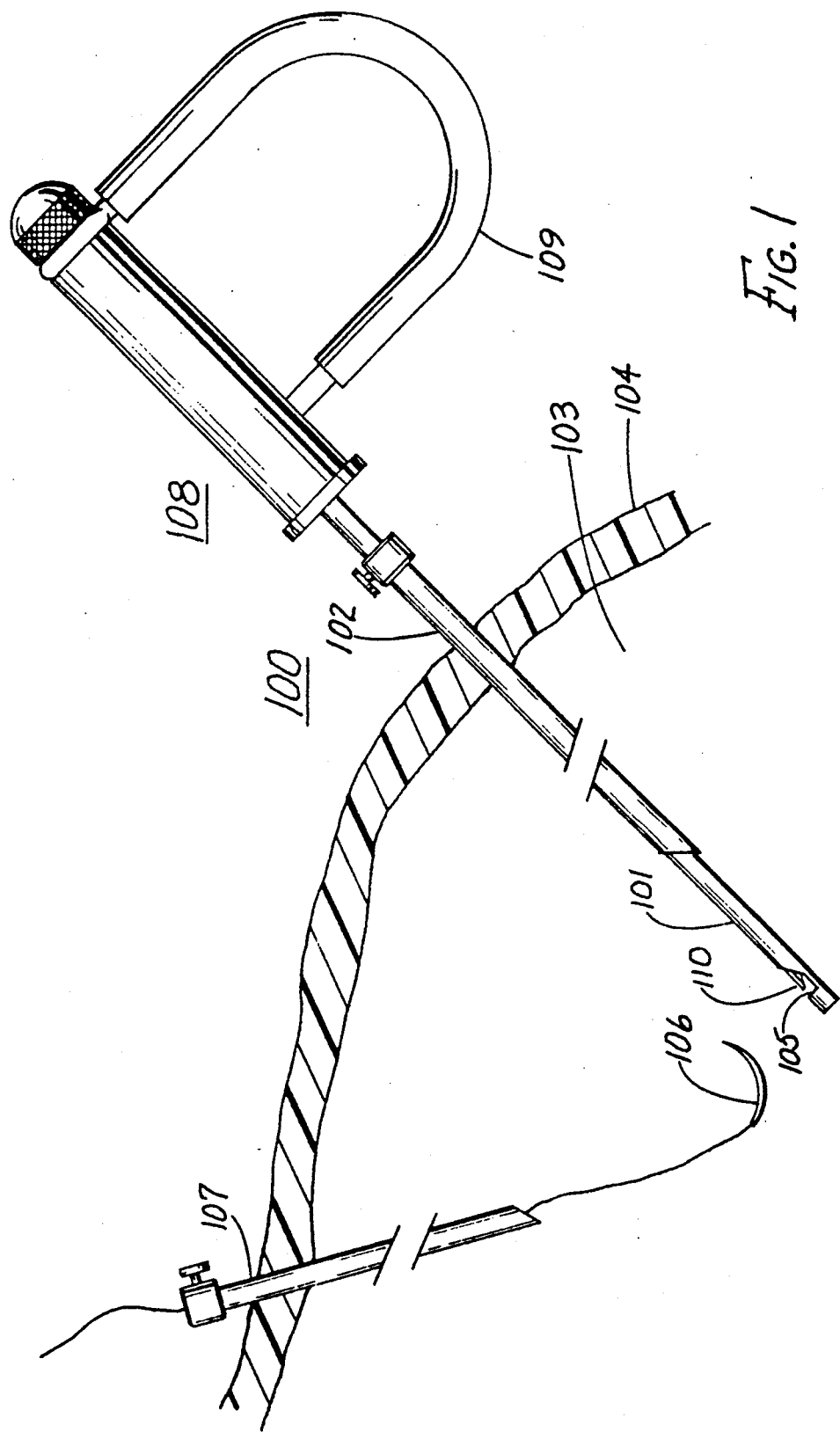
FIG. 1 depicts the needle driver instrument of the present invention inserted through a trocar sheath into a patient.

Depicted in FIG. 1 is medical instrument 100 such as a needle driver for driving a curved suture needle 106 through tissue to form sutures therein. The instrument includes an elongated member 101, such as a cylindrical tube, which is passed through the passageway of trocar sheath 102 and into the peritoneal cavity 103 of patient 104. The trocar sheath is inserted into the patient for performing a minimally invasive endoscopic surgical procedure such as an operative laparoscopic or pelviscopic procedure usually associated with the reproductive organs of a female patient. The distal end of the elongated member includes a channel 105 for receiving curved suture needle 106, which is inserted into the peritoneal cavity with the elongated member or alternatively via another trocar sheath 107. Suture thread is connected to one end of the curved needle for suturing tissue together or closing the end of a tube severed in surgery. Attached at the proximal end of elongated member tube 101 is handle 108 with a generally U-shaped spring 109 extending therefrom for manual operation by the surgeon. This spring is easily grasped between the thumb and fingers of the surgeon for operating a wedge 110 which operates across the channel for grasping and fixedly positioning the suture needle.

Depicted in FIG. 2 is a partial cross-sectional side view of distal end 201 of elongated member 101 of the needle driver instrument. Elongated member 101 comprises a 7-gauge stainless steel tube approximately 12" in length for insertion through a 5 mm trocar sheath. The outside diameter of a 7-gauge stainless steel regular wall tube is approximately 0.180" with an inside diameter of 0.150". A cylindrically shaped hollow passageway 202 extends the entire length of the tube along longitudinal axis 203. Channel 105 is transversely cut in tube 101 and through passageway 202. As shown, the channel is cut such that four surfaces 205–207 are formed in the semicylindrical wall. A first contact surface 205 is substantially parallel to longitudinal axis 203 at a depth of 0.115" from the opening of the channel or the outer surface of tube 101. Second contact surface 204 forms an approximately 60° angle with longitudinal axis 203 with one end of the surface at the opening of the channel approximately 0.230" from the extreme distal end 208 of the tube. First contact surface 205 is approximately 0.050" in length.

The third contact surface 206 of the channel is approximately 0.195" in length and rises to a height of approximately 0.010" from the opening of channel 105.

The fourth contact surface 207 of the channel rises at approximately a 45° angle with respect to the longitudinal axis to the outside surface of the elongated tube. The third and fourth contact surfaces 206 and 207 guide the curved suture needle 106 into position and/or contact with first and second contact surfaces 205 and 204 as shown. Suture needle 106 at a point approximately midpoint through its curvature exhibits an elliptically-shaped cross section 209 with a plurality of grooves 210 and 211 formed on the outer and inner arc surfaces of the needle, respectively.

Wedge 110 comprises elongated segment 214 and an engaging segment 212 with beveled surface 213. The engaging segment, such as a cylindrical rod or tube, is silver soldered to elongated segment 214, such as a cylindrical rod or linkage tube, which extends through passageway 202 of elongated tubular member 101 into the passageway of handle 108. Engaging segment 212 is approximately 0.50" in length and is comprised of 9-gauge regular wall tubing having an outside dimension of 0.148" with an inside diameter of 0.118". Beveled surface 213 forms an angle of approximately 14° with respect to the longitudinal axis of the elongated member. The use of a tube for engaging segment 212 provide two separate contact areas for engaging curved suture needle 106.

A second beveled surface 215 at approximately a 45° angle is formed at the distal end of the engaging segment to reduce the sharpness of the distal end of the engaging segment so as not to extend beyond the distal end of outer elongated tubular member 101 while in use. A circular radius 216 is formed at the very distal end of the engaging segment to prevent any possible injury or extension of the engaging segment from passageway 202.

Elongated segment 214 is a stainless steel rod approximately 12.625" in length with an outside diameter of 0.125".

When wedge 212 is operated toward the distal end of passageway 202 with curved suture needle 106 in channel 105, the outer surface of the suture needle makes contact and is wedged against channel contact surfaces 204 and 205 and beveled surface 213 of the wedge. A longitudinal force applied to the proximal end of the cylindrical rod forces the wedge toward the distal end of elongated member 101 wedging the suture needle in an approximate 90° orientation with respect to longitudinal axis 203 as shown. The angles, as specified, have been experimentally found to hold the suture needle with the greatest amount of force in the indicated, approximate right-angle orientation with respect to the elongated member. This orientation is preferred by surgeons performing operative laparoscopic procedures to enable them to form uniform sutures through the trocar sheath. However, the contact surface and beveled surface angles may be formed to provide the suture needle with any other side view angular orientation with respect to longitudinal axis 203.

Figure 4:
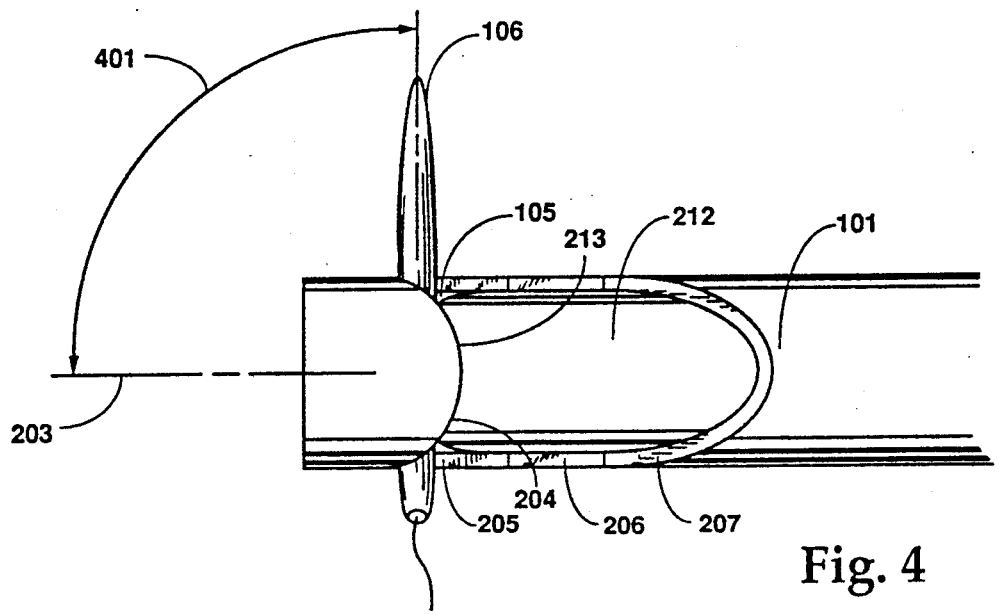
FIG. 4 depicts a top view of the distal end of the needle driver instrument of FIG. 1.

Depicted in FIG. 4 is a top view of the distal end of elongated member 101 with curved suture needle 106 wedged in channel 105. Engaging segment 212 of the wedge forces curved suture needle 106 into contact with contact surfaces 204 and 205 of channel 105 and beveled surface 213 of the wedge. When wedged into channel 105, needle 106 forms an angle 401 such as approximately 90° with respect to longitudinal axis 203 as viewed from the top. Angle 401 forms but just one orientation that has been experimentally found to be preferred by surgeons performing endoscopic surgical procedures.

Figure 5:
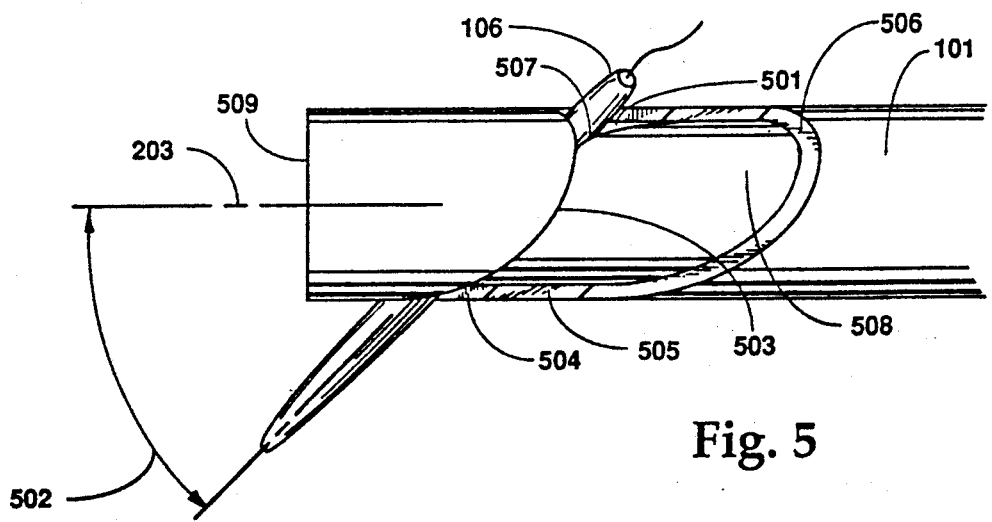
FIG. 5 depicts a top view of an alternative embodiment of the distal end of the needle driver instrument of FIG. 1.

Depicted in FIG. 5 is a top view of the distal end of elongated member 101 with curved suture needle 106 in an alternative embodiment channel 501. When wedged into alternative embodiment channel 501, needle forms an angle 502 such as approximately 45° with respect to longitudinal axis 203 as viewed from the top. Channel surfaces 503–506 are formed in elongated member 101 and beveled surface 507 of engaging segment 508 in the same manner as depicted in FIG. 4, except the channel and beveled surface are cut at a 45° rather than a 90° orientation. This 45° orientation causes the pointed end of the suture needle to extend beyond distal end 509 of the elongated member for extremely limited space applications or when the surgeon simply wants the needle point to extend beyond distal end 509 for suturing. Any top view angular orientation is contemplated. However, this 45° angular orientation has been experimentally found to be preferred by surgeons. Other combinations of top view and side view angular orientations are also contemplated depending on the preference of the surgeon.

Depicted in FIG. 3 is the proximal end of the instrument with handle 108 and generally U-shaped spring 109. The handle comprises a second elongated tubular member 301 having a passageway 302 positioned about longitudinal axis 203 extending from the first elongated tubular member 101. The second tubular member comprises a series 6061 T-6 drawn aluminum tube, rough tumbled and anodized blue in color having a 0.500" outside diameter and an inside diameter of 0.370". The tube is approximately 3.250" in length with a plurality of threads 303 and 304 formed in the inside surface of the tube. The distal threads 303 are approximately 0.375" in length, whereas proximal threads 304 extend approximately 0.500" into the proximal end of the tube. An elongated slot 305 is longitudinally formed in the wall of tube 301 approximately 1" in length and 0.1875" in width at a distance of 0.375" from the distal end 306 of the second elongated tubular member. The proximal end 307 of cylindrical rod 214 is inserted into a larger diameter cylindrical tube 308 and soldered therein using silver solder 309. Cylindrical tube 308 is a series 300 stainless steel tube approximately 1.5" in length with an outside diameter of 0.360" and an inside diameter of 0.128". Centered at approximately 0.750" from the distal end thereof is a 3/16" radial hole 327 extending to passageway 310 of the tube. The L-shaped distal end 311 of spring 109 is inserted through slot 305 of the handle tube and into the radial hole 327 of tube 308 for moving the wedge including rod segment 214 within the passageways of the handle and elongated members.

At the distal end of elongated cylindrical tube 101 is front cap 312 which screws into the passageway of tube handle 108. The proximal end of tube 101 is silver soldered to front cap 312. Front cap 312 is approximately 0.300" in length and is formed from type 301 stainless steel rod. The outside diameter of the cap is 0.625" with a 0.182" inside diameter passageway therethrough. A plurality of threads 314 such as 7/16-20 threads with a maximum outside dimension of 0.430" are formed therein.

End cap 313 is formed from a 0.500" diameter stainless steel rod. The rod is approximately 0.75" in length with a threaded portion of, for example, 7/16-20 threads formed at the distal end thereof. The threads are approximately 3/16" in length. A recess 318 of approximately 3/16" in length with a 0.300" diameter relief is formed therein to receive the proximal end 316 of the generally U-shaped spring which is formed into an eye around the relief area of the end cap. An internal passageway 319 of approximately 0.125" is drilled and counter sunk through the longitudinal axis of the rod. A knurled portion 320 of 0.32" is formed on the proximal end cap for turning the cap into the handle tube 108.

The generally U-shaped spring 109 of the handle is covered with a tubular plastic material 315 to facilitate easy handling of the spring. The surgical instrument is easily disassembled for cleaning and subsequent reuse due to the modular construction thereof. A similar medical instrument may be formed with 12-gauge tubing for the elongated member to facilitate use through a 3 mm trocar. In such instance, the channel formed at the distal end of the tube would start approximately 0.100" from the distal end with a maximum depth of 0.065" extending up to 0.053" for the start of the fourth contact surface. Parallel contact surface 210 would be approximately 0.050" in length with third contact surface 206 being 0.05" in length. These dimensions would facilitate the preferred angles for securing a smaller curved suture needle.

It is to be understood that the above-described medical instrument for driving a curved suture needle is merely an illustrative embodiment of the principles of this invention and that other apparatus may be devised by those skilled in the art without departing from the spirit and scope of this invention. In particular, the length and outside diameter of the elongated member may be varied to facilitate use in different sized trocar sheaths. This needle driver has also been described for use with a curved suture needle. However, the needle driver is also applicable for use with a straight needle having a proportionate cross-sectional diameter. It is also contemplated that a coil compression spring be inserted in the tubular handle to force the wedge against a suture needle inserted in the channel. The coil spring would be compressed and released via any one of a number of well-known, manually activated lever assemblies.

What is claimed is:

1. A medical instrument for driving a suture needle through tissue, comprising:
   an elongated member having a longitudinal passageway therein;
   a channel capable of receiving said needle and positioned in said elongated member about a distal end thereof and transverse through said passageway;
   a wedge positioned within said passageway and operable across said channel to secure said needle between said elongated member and said wedge when said needle is positioned in said channel; and
   a handle attached about a proximal end of said elongated member and having a longitudinal passageway extending to said longitudinal passageway of said elongated member.

2. The instrument of claim 1 wherein said wedge includes an elongated segment movable within said elongated member and handle passageways.

3. The instrument of claim 2 wherein said handle includes a spring having first and second ends at least one of which is connected to said elongated segment and capable of moving said elongated segment in said elongated member and handle passageways.

4. The instrument of claim 2 wherein said handle includes a spring having a first end connected to said elongated segment and capable of moving said elongated segment in said handle passageway and a second end connected to a proximal end of said handle.

5. A medical instrument for driving a suture needle through tissue, comprising:
   an elongated member having a longitudinal passageway therein;
   a channel capable of receiving said needle and positioned in said elongated member about a distal end thereof and transverse through said passageway; and
   a wedge having a beveled surface, positioned within said passageway and operable across said channel to secure said needle between said elongated member and said beveled surface of said wedge when said needle is positioned in said channel.

6. The instrument of claim 5 wherein said elongated member comprises a tube, said channel forming a predetermined number of channel surfaces in said tube each capable of making contact with said needle when said needle is positioned in said channel.

7. The instrument of claim 5 wherein said wedge includes an engaging segment having said beveled surface forming a predetermined angle with respect to a longitudinal axis of said elongated member, said beveled surface being capable of making contact with said needle when said needle is positioned in said channel.

8. The instrument of claim 7 wherein said engaging segment includes a tube having said beveled surface, said beveled surface having first and second contact areas with said needle when said needle is positioned in said channel means and said wedge means is operated through said channel means.

9. The instrument of claim 6 wherein said channel surfaces include a first channel surface forming a first predetermined angle with respect to a longitudinal axis of said tube.

10. The instrument of claim 9 wherein said channel surfaces include a second channel surface forming a second predetermined angle with respect to said longitudinal axis.

11. The instrument of claim 10 wherein said channel surfaces include a third channel surface forming a third predetermined angle with respect to said longitudinal axis.

12. The instrument of claim 10 wherein said channel surfaces include a fourth channel surface forming a fourth predetermined angle with respect to said longitudinal axis.

13. The instrument of claim 5 further comprising a handle attached about a proximal end of said elongated member.

14. The instrument of claim 13 wherein said handle includes a longitudinal passageway extending to said longitudinal passageway of said elongated member.

15. The instrument of claim 14 wherein said wedge includes an elongated segment moveable within said elongated member and handle passageways.

16. The instrument of claim 15 wherein said handle includes a spring having first and second ends at least one of which is connected to said elongated segment and capable of moving said elongated segment in said elongated member and handle passageways.

17. The instrument of claim 15 wherein said handle includes a spring having a first end connected to said elongated segment and capable of moving said elongated segment in said handle passageway and a second end connected to a proximal end of said handle.

18. A medical instrument for driving a curved suture needle, comprising:
   a first tube segment having a first longitudinal axis and distal and proximal ends and including a first longitudinal passageway therein along said first longitudinal axis;
   a channel capable of receiving said needle and positioned in said first tube segment about said distal end thereof and transverse through said first passageway, said channel forming a plurality of surfaces in said first tube segment, each capable of making contact with said needle when said needle is positioned in said channel;
   a second tube segment connected to said proximal end of said first tube and having a second passageway along said axis of said first tube segment;
   a wedge positioned within said first passageway and operable across said channel for fixedly positioning said needle between said channel surfaces and said wedge when said needle is positioned in said channel;
   a rod connected to said wedge and positioned in said first and second passageways;
   a spring connected to said rod in said second tube segment and manually operable for operating said wedge across said channel.

19. The instrument of claim 18 wherein said wedge comprises a third tube segment and having a beveled surface forming a predetermined angle with respect to said longitudinal axis, said beveled surface being capable of making contact with said needle when said needle is positioned in said channel.

20. The instrument of claim 19 wherein said channel surfaces include a first contact surface positioned substantially parallel to said longitudinal axis.

21. The instrument of claim 20 wherein said channel surfaces include a second contact surface positioned at a second predetermined angle with respect to said longitudinal axis, said needle forming a predetermined position angle with respect to said longitudinal axis when fixedly positioned in said channel between said first and second contact surfaces and said beveled surface.

22. The instrument of claim 21 wherein said channel surfaces include third and fourth contact surfaces capable of guiding said needle into contact with said first and second contact surfaces when said needle is positioned in said channel.

23. An endoscopic surgical instrument insertable through a trocar sheath for driving a suture needle, comprising:
   elongated means for inserting through said trocar sheath;
   channel means positioned in said elongated means and about a distal end thereof for receiving said needle; and
   wedge means having a beveled surface, positioned about a distal end of said elongated means and operable through said channel means for fixedly positioning said needle in said channel means between said elongated means and said beveled surface.

24. The instrument of claim 23 further comprising handle means positioned about a proximal end of said elongated means for positioning said elongated means and said channel means.

25. The instrument of claim 24 wherein said handle means includes control means for controlling the operation of said wedge means through said channel means.

26. The instrument of claim 23 wherein said channel means includes a plurality of contact surfaces for positioning said suture needle in a predetermined orientation with respect to said elongated means.

27. A medical instrument for driving a suture needle through tissue, comprising:

a tube having a longitudinal passageway therein;

a channel capable of receiving said needle and positioned in said tube about a distal end thereof and transverse through said passageway, said channel forming a predetermined number of channel surfaces in said tube each capable of making contact with said needle when said needle is positioned in said channel, a first of said channel surfaces forming a first predetermined angle with respect to a longitudinal axis of said tube, a second channel surface forming a second predetermined angle with respect to said longitudinal axis, and a third channel surface forming a third predetermined angle with respect to said longitudinal axis; and a wedge positioned within said passageway and operable across said channel to secure said needle between said tube and said wedge when said needle is positioned in said channel.

28. The instrument of claim 27 wherein said channel surfaces includes a fourth channel surface forming a fourth predetermined angle with respect to said longitudinal axis.

* * * * *